(12) United States Patent
Lamei et al.

(10) Patent No.: US 9,556,729 B2
(45) Date of Patent: Jan. 31, 2017

(54) ESTIMATING PERMEABILITY IN UNCONVENTIONAL SUBTERRANEAN RESERVOIRS USING DIAGNOSTIC FRACTURE INJECTION TESTS

(71) Applicants: Halliburton Energy Services, Inc., Houston, TX (US); Petro Research & Analysis Corp., Lubbock, TX (US)

(72) Inventors: Christopher Hoss Lamei, Wolfforth, TX (US); Mohamed Yousef Soliman, Lubbock, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 132 days.

(21) Appl. No.: 14/429,322

(22) PCT Filed: Feb. 19, 2014

(86) PCT No.: PCT/US2014/017202
§ 371 (c)(1),
(2) Date: Mar. 18, 2015

(87) PCT Pub. No.: WO2015/126388
PCT Pub. Date: Aug. 27, 2015

(65) Prior Publication Data
US 2016/0230547 A1   Aug. 11, 2016

(51) Int. Cl.
*E21B 49/00* (2006.01)
*E21B 33/12* (2006.01)
(Continued)

(52) U.S. Cl.
CPC ............. *E21B 49/008* (2013.01); *E21B 33/12* (2013.01); *E21B 43/26* (2013.01); *E21B 47/06* (2013.01); *G01N 15/08* (2013.01)

(58) Field of Classification Search
CPC .......... E21B 49/00; E21B 49/008; E21B 49/10
See application file for complete search history.

(56) References Cited

U.S. PATENT DOCUMENTS 7,054,751 B2   5/2006   Craig
7,448,262 B2   11/2008  Sheng et al.
(Continued)

OTHER PUBLICATIONS

Lamei et al., "New Before Closure Analysis Model for Unconventional Reservoirs," SPE 14UNC-167790-MS, Austria, Feb. 25-27, 2014, 16 pages.
(Continued)

*Primary Examiner* — Jennifer H Gay
*Assistant Examiner* — David Carroll
(74) *Attorney, Agent, or Firm* — John W. Wustenberg; Parker Justiss, P.C.

(57) ABSTRACT

In an example diagnostic fracture injection test (DFIT), or a "minifrac," a fracturing fluid is pumped at a relatively constant rate and high pressure to achieve a fracture pressure of a subterranean formation. Sometime after achieving formation fracture pressure, the pump is shut off and the well is shut in, such that the pressure within the sealed portion of the well equilibrates with the pressure of the subterranean formation. As the pressure declines, the pressure of the injection fluid is monitored. This collected pressure data is then used to determine information regarding the permeability of the subterranean formation. In some implementations, a model for before closure analysis (BCA) can be used to estimate the permeability of a formation based on before closure pressure data (i.e., data collected before the fracture closure pressure is reached) based on a solution to the rigorous flow equation of fracturing fluid, which is leaking off into the formation during fracture closure.

21 Claims, 9 Drawing Sheets

(51) Int. Cl.
E21B 43/26 (2006.01)
E21B 47/06 (2012.01)
G01N 15/08 (2006.01)

(56) References Cited

U.S. PATENT DOCUMENTS

| | | | |
|---|---|---|---|
| 2005/0216198 A1* | 9/2005 | Craig | E21B 49/008 702/12 |
| 2008/0210470 A1 | 9/2008 | Stewart | |
| 2009/0272528 A1 | 11/2009 | Voelker | |
| 2012/0298360 A1 | 11/2012 | Dalrymple et al. | |
| 2013/0205886 A1 | 8/2013 | Hegeman et al. | |

OTHER PUBLICATIONS

Zhou et al., "Production Forecasting and Analysis for Unconventional Resources," IPTC 17176, Beijiing, China, Mar. 26-28, 2013, 16 pages.

Lamei et al., "Revisiting the Before Closure Analysis Formulations in Diagnostic Fracturing Injection Test," SPE 163869, Society of Petroleum Engineers, Woodlands, Texas, Feb. 4-6, 2013, 13 pages.

Craig et al., "Application of a New Fracture-Injection/Falloff Model Accounting for Propagating, Dilated, and Closing Hydraulic Fractures," SPE 100578, Society of Petroleum Engineers, Canada, May 15-17, 2006, 17 pages.

Soilman et al., "After-Closure Analysis to Determine Formation Permeability, Reservoir Pressure, and Residual Fracture Properties," SPE 93419, Society of Petroleum Engineers, Bahrain, Mar. 12-15, 2005, 15 pages.

Abate et al., "Multi-precision Laplace transform inversion," International Journal for Numerical Methods in Engineering, 60;979-993, 2004, 16 pages.

Craig et al., "Adapting High Permeability Leakoff Analysis to Low Permeability Sands for Estimating Reservoir Engineering Parameters," SPE 60291, Society of Petroleum Engineers, Denver, CO, Mar. 2000, 9 pages.

Valko et al., "Fluid-Leakoff Delineation in High-Permeability Fracturing," SPE 56135-PA, Society of Petroleum Engineers, May 1999, 14 pages.

Fan, "A New Interpretation Model for Fracture-Calibration Treatments," SPE 37401-PA, Society of Petroleum Engineers, Jun. 1998, 7 pages.

Mayerhofer et al., "Pressure-Transient Analysis of Fracture-Calibration Tests," SPE 26527, Society of Petroleum Engineers, Mar. 1995, 6 pages.

Castillo, "Modified Fracture Pressure Decline Analysis Including Pressure-Dependent Leakoff," SPE 16417, Society of Petroleum Engineers, Denver, Colorado, May 18-19, 1987, 9 pages.

Soliman, "Analysis of Buildup Tests with Short Producing Time," SPE 11083, SPE Formation Evaluation Halliburton Services Research Center, Aug. 1986, 9 pages.

Nolte, "Determination of Fracture Parameters from Fracturing Pressure Decline," SPE 8341, 1979, 16 pages.

International Search Report and Written Opinion of the International Searching Authority issued in International Application No. PCT/US2014/017202 on Nov. 19, 2014; 12 pages.

* cited by examiner

ESTIMATING PERMEABILITY IN UNCONVENTIONAL SUBTERRANEAN RESERVOIRS USING DIAGNOSTIC FRACTURE INJECTION TESTS

CLAIM OF PRIORITY

This application is a U.S. National Stage of International Application No. PCT/US2014/017202, filed Feb. 19, 2014.

TECHNICAL FIELD

This invention relates to subterranean evaluation techniques, and more particularly to techniques for evaluating physical parameters of a subterranean reservoir using "minifrac" or diagnostic fracture injection tests (DFITs).

BACKGROUND

Unconventional subterranean formations (e.g., unconventional reservoirs) play an important role in hydrocarbon production. Unconventional reservoirs are continuous-type reservoirs containing large-scale reserves, including shale gas and shale oil reserves, coalbed methane (CBM), and tight gas reservoirs. Unlike conventional reservoirs, unconventional reservoirs require specialized production technology, such as massive fracturing treatments for shale reservoirs or dewatering CBM.

Extracting hydrocarbon from an unconventional reservoir can involve significant expenditures in several operational aspects. For example, for an extraction operation in a shale formation, notable costs are incurred relating to pressure pumping, contract drilling, line pipes, and drilling fluids. Before proceeding with these potentially massive and costly operations, production testing can be used to help operators better understand, analyze, and forecast production. Further, by better understanding the formation properties, operators can optimize simulated treatments, and design and implement more efficient and cost-effective treatments.

Understanding formation properties can be achieved by performing a variety of different types of tests. In addition to conventional well testing, other tests can be used to understand the mechanical properties of the rock, predict formation behavior, and to optimize hydraulic fracturing treatments. For example, fracture closure pressure, instantaneous shut-in pressure, fracture breakdown pressure, and the formation fracturing fluid leakoff coefficient can be determined using specialized tests before or after fracturing treatments. In another example, "minifrac" or diagnostic fracture injection tests (DFITs) can be used to estimate the permeability of a formation and the initial reservoir pressure.

DESCRIPTION OF DRAWINGS

Like reference symbols in the various drawings indicate like elements.

DETAILED DESCRIPTION

Figure 1:
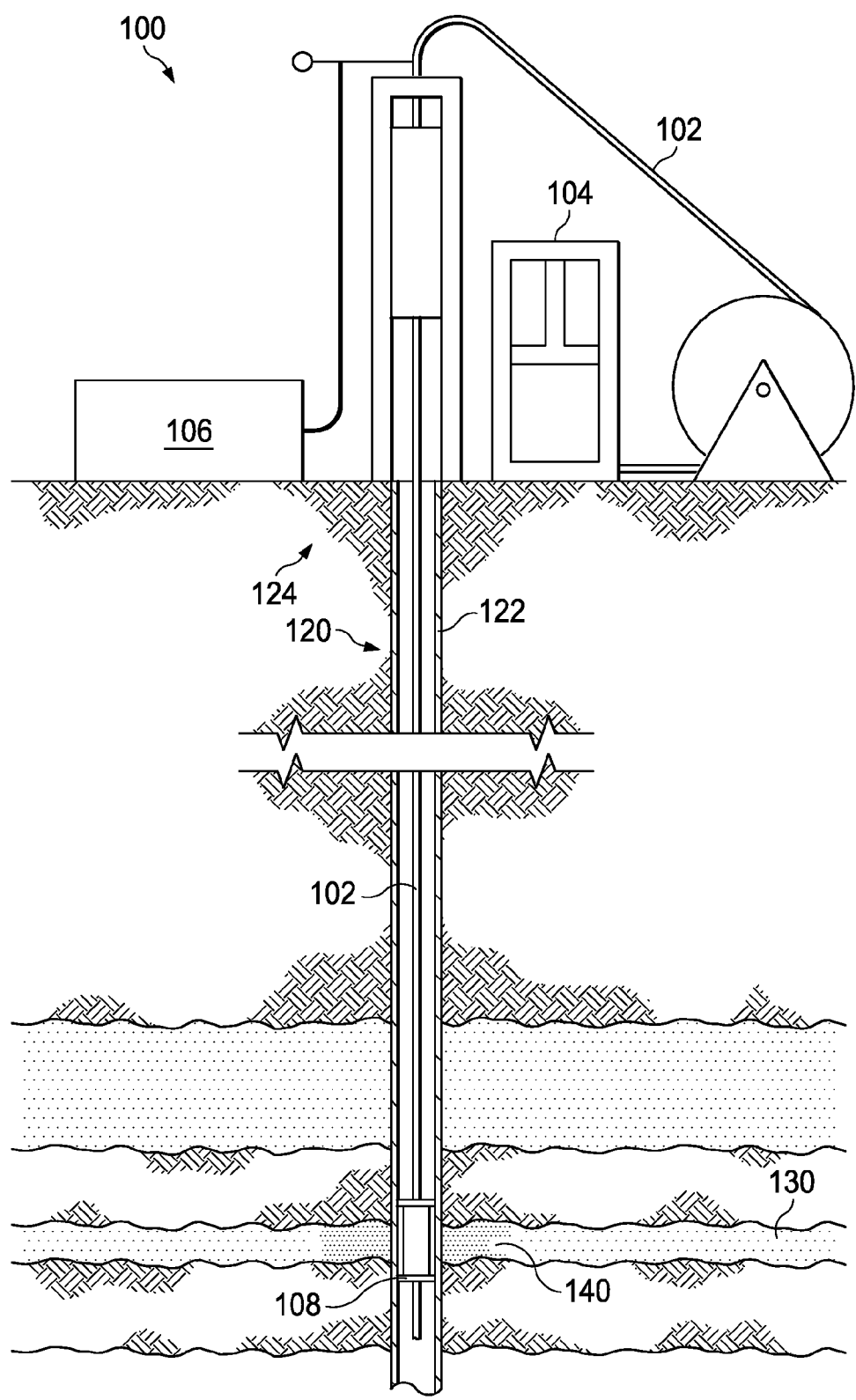
FIG. 1 is a diagram of an example system for performing a diagnostic fracture injection test (DFIT).

A diagnostic fracture injection test (DFIT), or a "minifrac," is a subterranean analysis technique in which a fracturing fluid is pumped at a relatively constant rate and high pressure to achieve a fracture pressure of a subterranean formation. FIG. 1 illustrates schematically an example system 100 for performing a DFIT on a subterranean region 130. System 100 includes a coiled tubing 102, a pump 104, a processing module 106, and one or more isolation packers 108. During use, coiled tubing 102 inserted into a wellhead 124 of a well 120, and suspended within the casing string 122 of the well 120.

Isolation packers 108 are arranged along the length of coiled tubing 102, and provide a seal between the coiled tubing 102 and the casing string 122. Isolation packers 108 can be moved downward or upward along coiled tubing 102 in order to create zonal isolation of a desired layer of subterranean region 130, such that the desired layer can be tested.

A hydraulic pump 104 is attached to the coiled tubing 102 in order to inject injection fluid into a subterranean region 130 (e.g., a subterranean reservoir) to test for an existing fracture or a new fracture 140. The pump can be a positive displacement pump, and can be used to inject either relatively small volumes (e.g., about 10-20 bbl) or relatively large volumes (e.g., about 70-80 bbl)) of injection fluids. Injection fluids can be compressible fluids (e.g., a gas, such as Nitrogen) or slightly compressible fluids (e.g., treated water, such as 2% KCl water with a surfactant).

Instrumentation for measuring the pressure of the reservoir and injected fluids (not shown) are arranged along the length of coiled tubing 102. Data can be collected by the instrumentation before, during and after the injection of injection fluid. This data can be collected continuously, intermittently, or periodically, as desired.

The data obtained by the measuring instruments are stored for later manipulation and transformation within the processing module 106 located on the surface. Data can be transmitted between the instrumentation and the processing module 106 by any conventional telemetry system.

Figure 2:
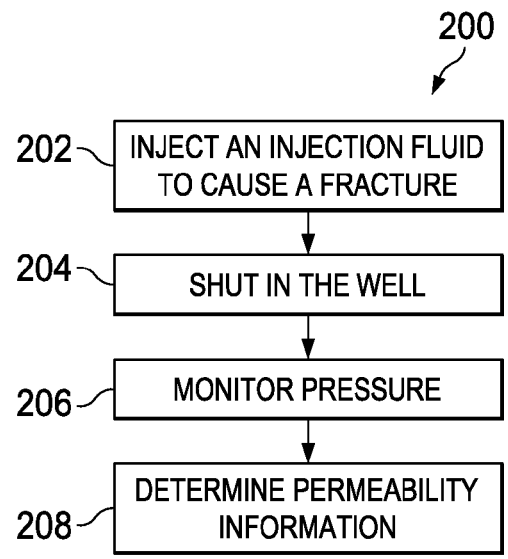
FIG. 2 is a flow chart of an example method of performing a DFIT.

An example method 200 of using system 100 to perform DFIT is shown in FIG. 2. In method 200, an injection fluid is injected into a subterranean formation at an injection pressure sufficient to cause a fracture of the subterranean formation (202). The volume and the pressure of the injection fluid can vary depending on the implementation. In an example, a volume of 10-20 bbl injection fluid is injected into a subterranean formation at an injection pressure of approximately 5000-10000 psi, resulting in a fracture. During the pumping of injection fluid, the fracture will propagate and a portion of fracturing fluid will leak off into the formation.

Sometime after achieving formation fracture pressure (e.g., approximately 5000-10000 psi), the pump is shut off and the well is shut in (i.e., the well is sealed from the surface) (204), such that the pressure within the sealed portion of well equilibrates with the pressure of the subterranean formation. In an example, shut in can be performed by sealing the well at the wellhead (e.g., by sealing wellhead 124 of wellbore 120). After shut in, the pressure inside the fracture begins declining as the pumping is ceased the fracture beings to close. The between the end of shut in and the closure of the fracture can vary depending on the implementation, the formation type, and fluid volume, and other factors. In an example, the time between shut in and closure of the fracture can range from approximately 10 minutes (e.g., in the case of some high-permeability reservoirs) to 3000 minutes (e.g., in the case of some low-permeability, nanodarcy reservoirs).

As the pressure declines, the pressure of the injection fluid is monitored (206). In an example, instrumentation of system 100 can be used to collect pressure data before, during and after the injection of injection fluid, and can collect data continuously, intermittently, or periodically, as desired. This collected pressure data can be divided into two distinct regions: before closure pressure data and after closure pressure data, which are temporally separated by the point in time when the fracture closure pressure is reached. Pressure data from one or both regions can be collected for analysis.

This collected pressure data is then used to determine information regarding the permeability of the subterranean formation (208). Different analysis models can be used to interpret the collected pressure data. A suitable analysis model can be selected based on various factors, such as based on known or assumed information about the subterranean formation, the region of the pressure data being analyzed (i.e., whether the pressure data is before closure data vs. after closure data), or other considerations. For instance, in some implementations, a first analysis model can be used to interpret the before closure pressure data, and a different analysis model can be used to interpret after closure pressure data.

A model for before closure analysis (BCA) can be used to estimate the permeability of a formation based on before closure pressure data (i.e., data collected before the fracture closure pressure is reached) based on a solution to the rigorous flow equation of fracturing fluid, which is leaking off into the formation during fracture closure. Leakoff into unconventional formations follows the linear flow pattern attributed to the tight nature of the formation and low permeability. A solution is then developed based on the idea of the short time injection of the DFIT test relative to total time of the test, with the DFIT test considered as a whole, with no separation of injection and shut in time. The governing effects of injection and shut-in time are included in boundary conditions.

The flow equation in linear form can be written as follows:

$$\frac{\partial^2 P_D}{\partial x_D^2} = \frac{\partial P_D}{\partial t_D}, \quad (1)$$

where $P_D$ is dimensionless pressure, $x_D$ is the spatial dimensionless parameter of fracture of the fracture, and $t_D$ is dimensionless time.

The general solution for this equation is:

$$\bar{P}_D = c_1 e^{-x_D\sqrt{z}} + c_2 e^{x_D\sqrt{z}} \quad (2)$$

where $\bar{P}_D$ is the Laplace transform of $P_D$, $c_1$ and $c_2$ are constants, and z is the Laplace variable. The boundary and initial conditions for Eq. 2 are defined as:

$$B.Cs: \begin{cases} C_{Df}\frac{\partial P_{DS}}{\partial t_D} - \frac{\partial P_D}{\partial t_D}\Big|_{x_D=0} = 1 - U(t_D - t_{iD}), t_D > 0 \\ P_{DS} = P_D - S\frac{\partial P_D}{\partial x_D}\Big|_{x_D=0} \end{cases}$$

and:

I.C: $P_D = 0|_{x_D, t_D = 0}$, where $C_{Df}$ is the dimensionless fracture storage coefficient of the formation, $t_{iD}$ is the dimensionless time at the end of injection, U(t) is a unit function that is zero when $t < t_{Di}$, and 1 when $t \geq t_{Di}$, and S is the skin factor. $C_{Df}$ can be calculated using the following relations:

$$C_{Df} = \frac{0.8936 C_{bc}}{\phi c_t h L_f^2}, \quad (3)$$

where $C_{bc}$ is the before closure storage, $c_t$ is the total reservoir compressibility (expressed in dimension $M^{-1}LT^2$, where M is a dimension of mass), h is the fracture height, expressed in dimension L, and $L_f$ is the fracture length (expressed in dimension L). $C_{bc}$ can be defined depending on different fracture geometries (e.g., a Perkins-Kern-Nordgren (PKN) geometry, a Kristonovich-Geertsma-Daneshy (GDK) geometry, or a radial geometry). Table 1 defines $C_{bc}$ of each of three example fracture geometries, where v is Poisson's Ration (dimensionless), $x_f$ is the fracture length (expressed in dimension L), $h_f$ is the fracture height (expressed in dimension L), and E is the Young's modulus (expressed in dimension $ML^{-1}T^{-2}$):

TABLE 1

$C_{bc}$ VALUES FOR DIFFERENT GEOMETRIES

| PKN | GDK | Radial |
|---|---|---|
| $C_{bc} = \frac{\pi(1-v^2)x_f h_f^2}{5.615E}$ | $C_{bc} = \frac{\pi(1-v^2)h_f x_f^2}{5.615E}$ | $C_{bc} = \frac{16(1-v^2)R_f^3}{3 * 5.615E}$ |

By applying the initial condition, the solution for $c_2$ will be:

$$\lim_{t_D \to 0} P_D = \lim_{z \to \infty} z\bar{P}_D = 0 \to c_2 = 0. \quad (4)$$

And, by applying the boundary conditions:

$$C_{Df}\frac{\left(P_D - S\frac{\partial P_D}{\partial x_D}\right)}{\partial t_D} - \frac{\partial P_D}{\partial x_D}\bigg|_{x_D=0} = 1 - U(t_D - t_{iD}). \quad (5)$$

This equation could be solved by transferring into Laplace space. Taking Laplace from both sides of the above equation results in:

$$C_{Df}z\overline{P}_D - C_{Df}S\frac{\partial \overline{P}_D}{\partial x_D \partial t_D} - \frac{\partial \overline{P}_D}{\partial x_D}\bigg|_{x_D=0} = \frac{1}{z} - \frac{e^{-t_{iD}z}}{z}. \quad (6)$$

By substituting the $\overline{P}_D$ into the equation, the above equation can be written in the form of:

$$C_{Df}zc_1 e^{-x_D\sqrt{z}} + C_{Df}S z\sqrt{z}\, c_1 e^{x_D\sqrt{z}} + \quad (7)$$

$$\sqrt{z}\, c_1 e^{-x_D\sqrt{z}}\bigg|_{x_D=0} = \frac{1}{z} - \frac{e^{-t_{iD}z}}{z}$$

By applying $x_D=0$, the $c_1$ value could be written in the following form:

$$c_1 = \frac{1 - e^{-t_{iD}z}}{z(C_{Df}z + \sqrt{z}\,(C_{Df}Sz + 1))} \quad (8).$$

Consequently, the pressure solution on the fracture side will be:

$$\overline{P}_D = c_1 e^{-x_D\sqrt{z}} = \frac{(1 - e^{-t_{iD}z})e^{-x_D\sqrt{z}}}{z(C_{Df}z + \sqrt{z}\,(C_{Df}Sz + 1))} \quad (9).$$

The pressure solution on the formation side, considering the skin effect, can be found using the following relation between fracture side pressure and formation side pressure:

$$\overline{P}_{DS} = \overline{P}_D - S\frac{\partial \overline{P}_D}{\partial x_D}\bigg|_{x_D=0} \quad (10).$$

$$= \frac{(1 - e^{-t_{iD}z})}{z(C_{Df}z + \sqrt{z}\,(C_{Df}Sz + 1))} +$$

$$\sqrt{z}\,S\frac{(1 - e^{-t_{iD}z})}{z(C_{Df}z + \sqrt{z}\,(C_{Df}Sz + 1))}$$

And, finally, the fracture side pressure solution could be simplified as the following equation:

$$\overline{P}_{DS} = \frac{(1 - e^{-t_{iD}z})(1 + \sqrt{z}\,S)}{z(C_{Df}z + \sqrt{z}\,(C_{Df}Sz + 1))} \quad (11).$$

This equation can be solved in linear form in the case of unconventional reservoirs, where linear flow for leakoff liquid exists. The radial form of the equation also can be solved in the same format.

This BCA model is based on solving the fluid flow equation for the leakoff fluid into the formation. The Laplace transform of the leakoff rate into the formation, $\overline{q}_{DS}$, is defined according to the following equation:

$$\overline{q}_{DS} = zC_{Df}\overline{P}_{DS} = \quad (12).$$

$$\frac{zC_{Df}(1 - e^{-t_{iD}z})(1 + \sqrt{z}\,S)}{z(C_{Df}z + \sqrt{z}\,(C_{Df}Sz + 1))} = \frac{C_{Df}(1 - e^{-t_{iD}z})(1 + \sqrt{z}\,S)}{(C_{Df}z + \sqrt{z}\,(C_{Df}Sz + 1))}$$

This is the fluid leakoff equation, which can be inverted from Laplace space numerically. For simplicity, in some implementations, the skin factor can be ignored and can be assumed that the fracturing fluid has the same properties as the formation fluid. When the injecting fluid is liquid into a gas reservoir, there is a moving interface between leakoff liquid and formation fluid. However, when the injection volume is small, and assuming that the displacement is piston-like, the single phase model can be applied. A more comprehensive solution when considering the skin factor requires a more complex mathematical method to calculate the Laplace inverse of the fluid leakoff equation. For the purpose of this description, the skin factor is ignored; thus, the resulting equation for the fluid leakoff becomes:

$$\overline{q}_D = zC_{Df}\overline{P}_D = \frac{C_{Df}(1 - e^{-t_{iD}z})}{(C_{Df}z + \sqrt{z}\,)}. \quad (13).$$

The long-term approximation of Eq. 13 is:

$$\overline{q}_{DS} = -C_{Df}t_{iD}\sqrt{z} \quad (14)$$

Taking the Laplace inversion from both sides using Laplace pseudo-transform results in the following equation for fluid leakoff into the formation. The linear and radial solution of the long-term approximation will have fairly close results at the end:

$$q_D = \frac{C_{Df}t_{iD}}{2\sqrt{\pi t_D^3}}, \quad (15)$$

where $q_D$ is the dimensionless leakoff rate through one side of the fracture.

Assuming the dimensionless fluid leakoff for one side of the fracture is $$\frac{141.2\,\mu q}{kh\Delta P_{inj}},$$

where $\mu$ is the viscosity, q is the leakoff rate through one side (expressed in dimension $L^3T^{-1}$), the dimensional form of the Eq. 15 is:

$$q = \frac{C_{Df}t_{iD}}{2\sqrt{\pi t_D^3}}\frac{kh(P_{inj} - P_{initial})}{141.2\,\mu}, \quad (16)$$

where k is the reservoir permeability (expressed in dimension $L^2$) and $P_{initial}$ is the initial reservoir pressure.

On the contrary, by using material balance, fluid leakoff could be written as:

$$q = -A_f \frac{dw}{dt}, \quad (17)$$

where $A_f$ is the fracture area for one face (expressed in dimension $L^2$) and w is the fracture width (expressed in dimension L).

Substituting for fracture width with $c_f(P-P_c)$, where $P_c$ is the closure pressure (expressed in dimension $ML^{-1}T^{-2}$), one can write the new equation for leakoff according to Eq. 18:

$$q = -A_f c_f \frac{dP}{dt} \quad (18).$$

Equalizing Eq. 18 with the previous relation for fluid leakoff in Eq. 16, one can simplify the relation as follows:

$$q = \frac{C_{Df} t_{iD}}{2\sqrt{\pi t_D^3}} \frac{kh\Delta P_{inj}}{141.2 \, \mu} \frac{24}{5.615} = -A_f c_f \frac{dP}{dt}, \quad (19)$$

where $\Delta P_{inj}$ is the change in pressure at the end of injection.

By further simplifying the equation, the above relation becomes:

$$\frac{1}{\sqrt{\pi}} \frac{24}{141.2 * 5.615} \frac{kh\Delta P_{inj} C_{Df} t_i}{A_f c_f \mu} \left(\frac{\emptyset \mu c_t l^2}{0.000264 k}\right)^{1/2} \frac{-dt}{2\sqrt{t^3}} = dP, \quad (20)$$

where l is the fracture length (expressed in dimension L).

Replacing the fracture area, $A_f = h_f L_f$ for one side of the fracture, one can write the following equation. In all following examples, radial geometry calculations are only estimations, since fracture area calculation is different in this case.

$$1.051114 \frac{r_p \Delta P_{inj} C_{Df} t_i}{c_f} \left(\frac{\emptyset k c_t}{\mu}\right)^{\frac{1}{2}} \frac{-dt}{2\sqrt{t^3}} = dP, \quad (21)$$

where $r_p$ is the ratio of permeable area to fracture area and $\emptyset$ is the porosity.

Taking integral from both sides from the time of injection to the time step n, where n is any time step after injection time and before closure time, Eq. 21 could be written as $$1.051114 \frac{r_p \Delta P_{inj} C_{Df} t_i}{c_f} \left(\frac{\emptyset k c_t}{\mu}\right)^{\frac{1}{2}} \int_{t_i}^{t_n} \frac{-dt}{2\sqrt{t^3}} = \int_{t_i}^{t_n} dP, \quad (22)$$

where $t_n$ is the time at the end of step n (expressed in dimension T).

Solving for the integral, one gets the final form of the new BCA model.

$$1.051114 \frac{r_p \Delta P_{inj} C_{Df} t_i}{c_f} \left(\frac{\emptyset k c_t}{\mu}\right)^{\frac{1}{2}} \left(\frac{1}{\sqrt{t_n}} - \frac{1}{\sqrt{t_i}}\right) + P_i = P_n, \quad (23)$$

where $P_i$ and $P_n$ are the pressures P at time $t_i$ and $t_n$, respectively, and where the value of the fracture compliance $c_f$ (expressed in dimension $M^{-1}L^2T^2$) is listed in Table 2 for each of the three example fracture geometries, where $h_f$ is the fracture height (expressed in dimension L), $L_f$ is the fracture length (expressed in dimension L), $R_f$ is the fracture radius (expressed in dimension L), and E' is the plane strain modulus (expressed in dimension $ML^{-1}T^{-2}$):

TABLE 2

| $S_f$ VALUES FOR DIFFERENT GEOMETRIES | | |
|---|---|---|
| PKN | GDK | Radial |
| $c_f = \frac{\pi h_f}{2E'}$ | $c_f = \frac{\pi L_f}{E'}$ | $c_f = \frac{16 R_f}{3\pi E'}$ |

This equation shows that if one plots the falling pressure during the before closure period versus the time difference term in parenthesis, the results should fall on the straight line with the intercept showing the pressure at stopping the injection. The slope, M, of the resulting line will be equal to:

$$1.051114 \frac{r_p \Delta P_{inj} C_{Df} t_i}{c_f} \left(\frac{\emptyset k c_t}{\mu}\right)^{\frac{1}{2}} = M \quad (24).$$

Solving for the permeability of the formation provides the following term for calculating the permeability of formation $$k = \left(\frac{0.9514 M c_f}{r_p \Delta P_{inj} C_{Df} t_i}\right)^2 \left(\frac{\mu}{\emptyset c_t}\right) \quad (25).$$

Figure 3:
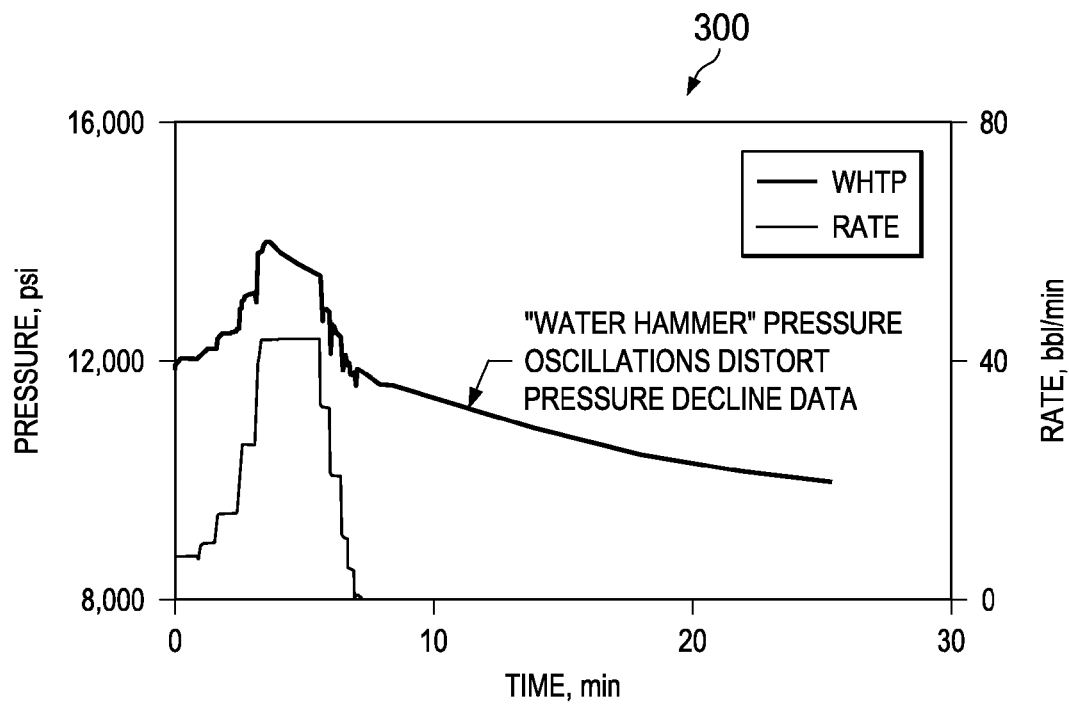
FIG. 3 is a plot of pressure versus time data obtained for a DFIT of an example formation.
Figure 4:
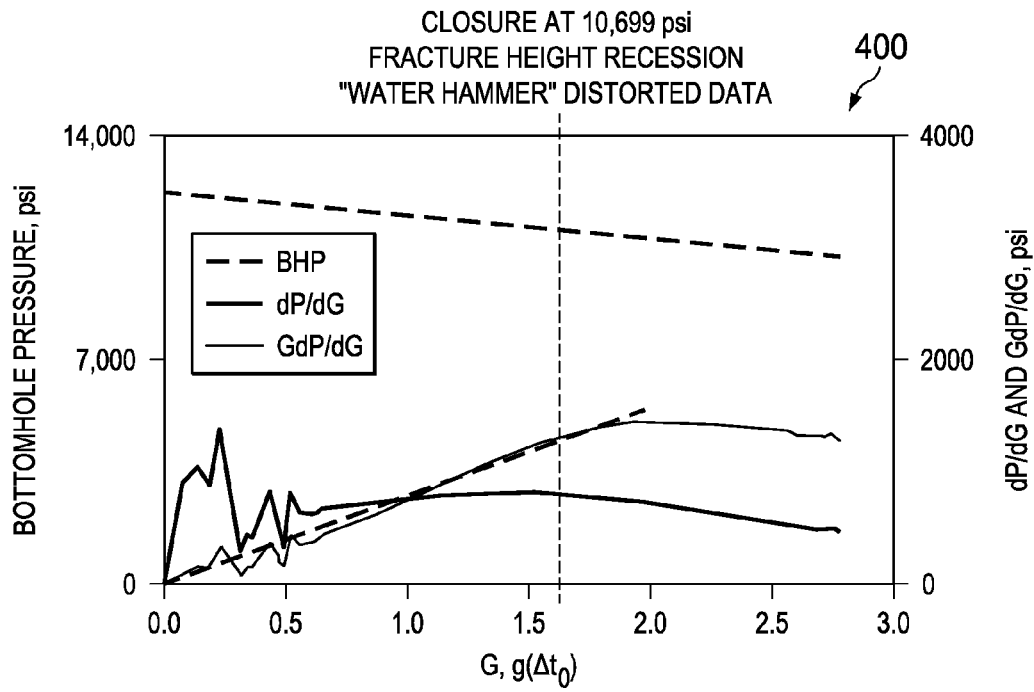
FIG. 4 is a plot of the G-function for the example formation.

This relation shows that the formation permeability can be calculated using the before closure data, and the properties of the formation. This model is based on solving the rigorous fluid equation for unconventional reservoirs with linear flow, and does not require any limiting assumptions that can interfere with interpretation of the results. Thus, this BCA model can be used to examine an unconventional reservoir more accurately, without relying on accurate estimates, limiting assumptions, or additional a priori information that may unavailable or impractical to determine for a particular application. In some implementations, the solution for other types of flow, for example radial flow, can also be derived in the same manner. Further, as no limiting assumptions are required, this BCA model can be used to examine a broad range of unconventional reservoirs under a broad range of conditions. For instance, this BCA model can used to analyze a variety of different formations. As an example, pressure data versus time (i.e., wellhead treating pressure (WHTP)) and injection fluid injection rate for an example formation is shown in plot 300 of FIG. 3. There is some "water hammer" right after shut-in time, which resulted in distorting the WHTP data shortly after shut-in. The G-function plot 400 is shown in FIG. 4, which shows the borehole pressure (BHP) at the point of fracture closure (i.e., the fracture closure pressure) is equal to 10,699 psi, and closure time is 411 sec after the end of injection.

The effect of pressure-dependent leakoff (PDL) in early time, and fracture height recession is clear in the G-function plot. In this example, the water hammer effect on pressure was manually minimized; but, the overall effect of height recession is clear in the data. Height recession occurs when fractures closes at high-stress impermeable layers, and the total fracture area starts approaching to the permeable fracture area. Although, this effect distorts the pressure data, BCA could still be performed as long as there are enough pressure data in normal leakoff situations. After plotting the before closure plot, these effects are clearly seen. This DFIT test represents the of injection of 7,375 gal of fracturing fluid for 422 sec. The average injection rate was 16.2 bbl/min. The instantaneous shut-in pressure (ISIP) was also recorded as 11,894 psi. Physical formation and fracture properties are listed in Table 3. Fracture length is listed for three different fracture geometries as well. In this example, the formation thickness is 40 ft (30 ft of net) and the bottomhole temperature (BHT) was 300° F. The estimated kh for this well using prefracturing analysis was 86 md-ft.

TABLE 3

FORMATION AND FRACTURE PROPERTIES
Formation Properties

| | | |
|---|---|---|
| $c_t$ | 6.35E−05 | $psi^{-1}$ |
| $\mu_f$ | 0.0203 | cp |
| Porosity | 0.12 | |
| Poisson's | 0.2 | |
| E | 5.00E+06 | psi |
| $P_c$ | 10,699 | psi |
| $h_p$ (permeable height) | 30 | ft |
| $h_f$ | 40 | ft |
| $X_f$ (GDK) | 87 | ft |
| $X_f$ (PKN) | 70 | ft |
| $R_f$ (Radial) | 72 | ft |

As it could be seen from plot 400, showing an implementation of the present BCA model formulation, the ISIP also could be calculated using this model. $P_{inj}$ is the pressure at the end of pumping, which, according to the Eq. 23, will be the intercept of the straight line with the pressure axis. The time term in Eq. 23 will result in negative numbers as time increases from injection time of $t_i$ to any point after shut-in time and before closure time of $t_c$.

Figure 5:
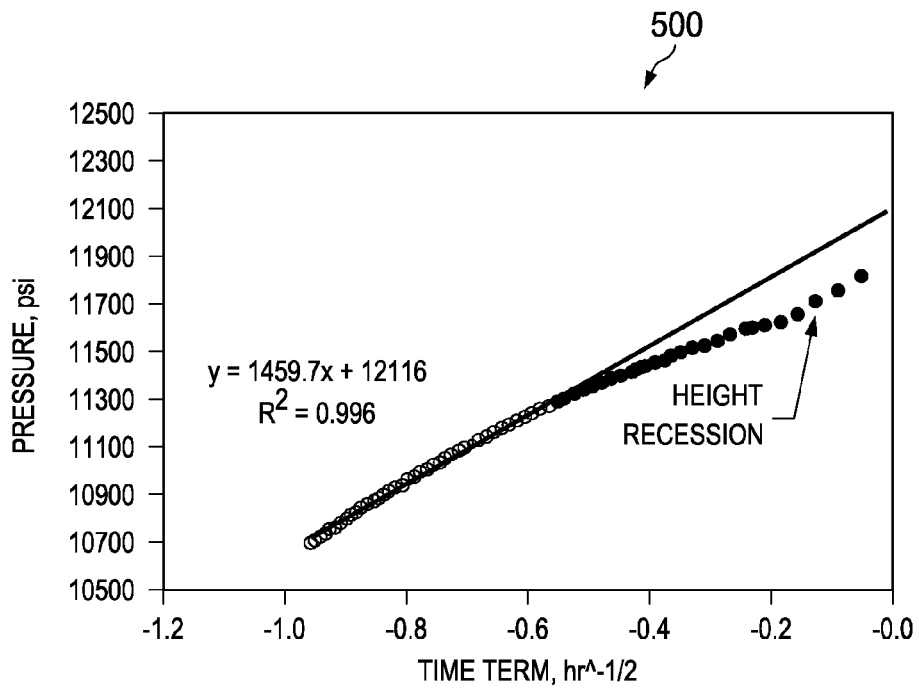
FIG. 5 is a plot of an example implementation of a before closure analysis (BCA) model.

Referring to FIG. 5, the BCA plot 500 corresponds to a plotting of $(P_i - P_n)$ versus time term of $$\left(\frac{1}{\sqrt{t_n}} - \frac{1}{\sqrt{t_i}}\right)$$

in Eq. 23. As it can be seen in the BCA plot 500, the height recession effect caused the data not to fall on the straight line. Once the normal leakoff period was achieved, the data began falling on straight line. The slope of the straight line is calculated as 1459.7 $psi*hr^{1/2}$ and the intercept is calculated as 12,116 psi. The few points between the end of the height recession effect and the start of normal leakoff were not considered. However, in some implementations, this method can be considered as a more reliable tool for estimating the ISIP.

By using the slope of the straight line, the calculation of the permeability of the formation could be performed as follows:

$$1.051114 \frac{r_p \Delta P_{inj} C_{Df} t_i}{c_f} \left(\frac{\phi k c_t}{\mu}\right)^{\frac{1}{2}} = 1459.7 \; psi*hr^{1/2}.$$

$\Delta P_{inj}$ is calculated by using the intercept of the straight line and initial pressure pressure equal to 3,776 psi, and $r_p = 0.75$. The calculation of permeability for the three different example fracture geometries of GDK, PKN, and radial is listed in Table 4:

TABLE 4

RESULTS FOR NEW BCA MODEL

| Fracture Geometry | Storage Coefficient | Cd | Cf | K md |
|---|---|---|---|---|
| PKN | 1.20E−02 | 9.60E−03 | 1.21E−05 | 0.07 |
| GDK | 3.29E−02 | 1.68E−02 | 5.28E−05 | 0.46 |
| Radial | 6.81E−02 | 5.13E−02 | 2.35E−05 | 0.01 |

The permeability calculated for three geometries range from 0.01 to 0.46 md. To confirm this calculation, ACA is also provided and the results were also compared to a modified Mayerhofer's model. The initial pressure used for BCA was given in data equal to 8,340 psi and was used in before closure analysis. However, in ACA, the initial pressure could be calculated as shown below.

ACA analysis requires knowledge of the reservoir initial pressure. In this example, this reservoir pressure was determined to be 8,765 psi by a pre-fracturing analysis, and also was determined by using the Cartesian plot of the pressure and its derivative versus reciprocal of time.

After finding the initial reservoir pressure, and plotting the log-log graph of pressure and its derivative versus reciprocal of time, the ACA can be conducted.

Figure 6:
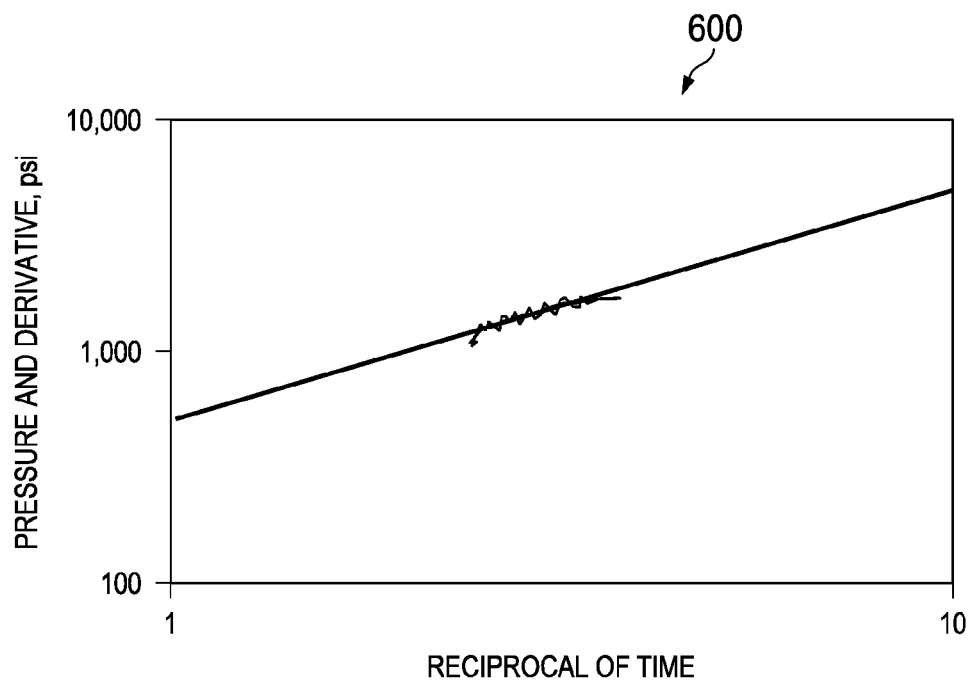
FIG. 6 is a log-log plot of an example after closure analysis (ACA) model.

The derivative plot 600 is shown in FIG. 6, and indicates the unit slope, which is indicative of the presence of pseudo-radial flow. Radial flow occurs when a fracture is closed, and the formation controls the fluid flow patterns. In the log-log graph in FIG. 6, two lines overlap with a slope of 1, and the intercept of the log-log plot was used to calculate the formation permeability. The radial flow equation could be written in the following form:

$$P_{fo} - P_i = \frac{1694.4 \, V\mu}{kh} \frac{1}{(t_i + \Delta t)}, \quad (26)$$

and the formation permeability by using intercept of log-log graph is:

$$kh = \frac{1694.4 \, V\mu}{b_r} \quad (27).$$

Substitution of the values into the above equation results in calculation of kh equal to 11.25 md-ft $$kh = \frac{1694.4 \left(\frac{7375}{42}\right) * 0.02}{500} = 11.25 \quad (28).$$

Considering the reservoir net thickness of 30 ft, the permeability is calculated as 0.38 md. This value is very close to 0.46 md calculated with the present before closure model for GDK geometry, which indicates that the best geometry to describe the fracture in this example is GDK. The radial geometry for before closure results shows significantly lower permeability and PKN resulted in lower formation permeability as well.

The slight difference of 0.08 md between the BCA and ACA may be caused by the estimated value of Young's Modulus when calculating the fracture length using Nolte-Shlyapobersky model and the difference in initial pressure.

Figure 7:
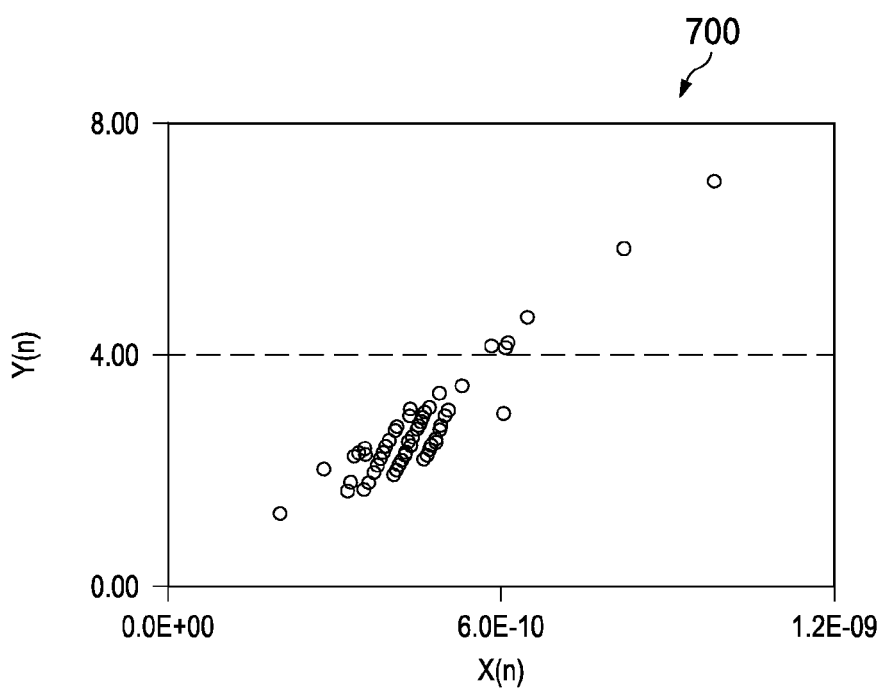
FIG. 7 is a plot of a modified Mayerhofer's BCA model.

This example showed the application of the present BCA for estimation of permeability. To further confirm the reliability of this new model, the results also were compared to the BCA developed using a modified Mayerhofer's model. It should be noted that, according to the assumptions of developing the modified Mayerhofer's model, the normal leakoff points should fall on a straight line. Plot 700 of FIG. 7 illustrates the modified Mayerhofer's BCA model for only GDK geometry. The scattering of data shows the PDL and height recession effect on the data. The results from this model are shown in Table 5.

TABLE 5

MODIFIED MAYERHOFER'S MODEL
PERMEABILITY CALCULATION

| Fracture Geometry | K md |
|---|---|
| PKN | 0.01-0.04 |
| GDK | 0.02-0.09 |
| Radial | 0.03-0.06 |

Figure 8:
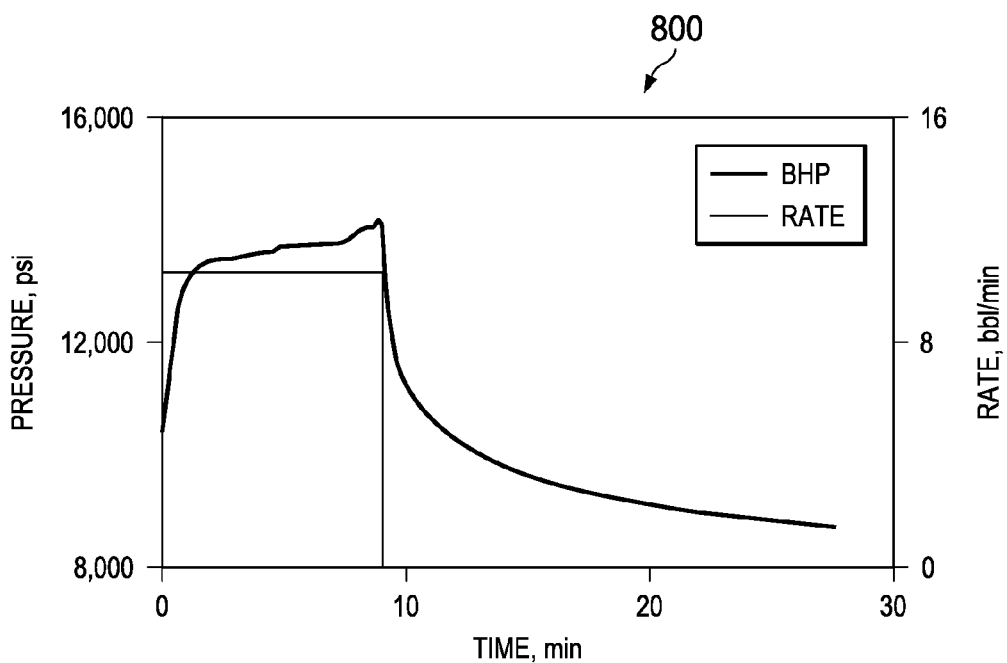
FIG. 8 is a plot of pressure versus time data obtained for a DFIT of a second example formation.

In another example, plot 800 of FIG. 8 illustrates pressure falloff data versus time in the DFIT test of another example formation. In this example, the formation is a tight formation with relatively low porosity.

This test represents of injection of 7,966 gal of fluid for 1,090 sec. The injection rate was 10.5 bbl/min. The closure was at 11,505 psi and the closure time was 90 sec after the end of injection. ISIP was recorded at 13,508 psi.

Figure 9:
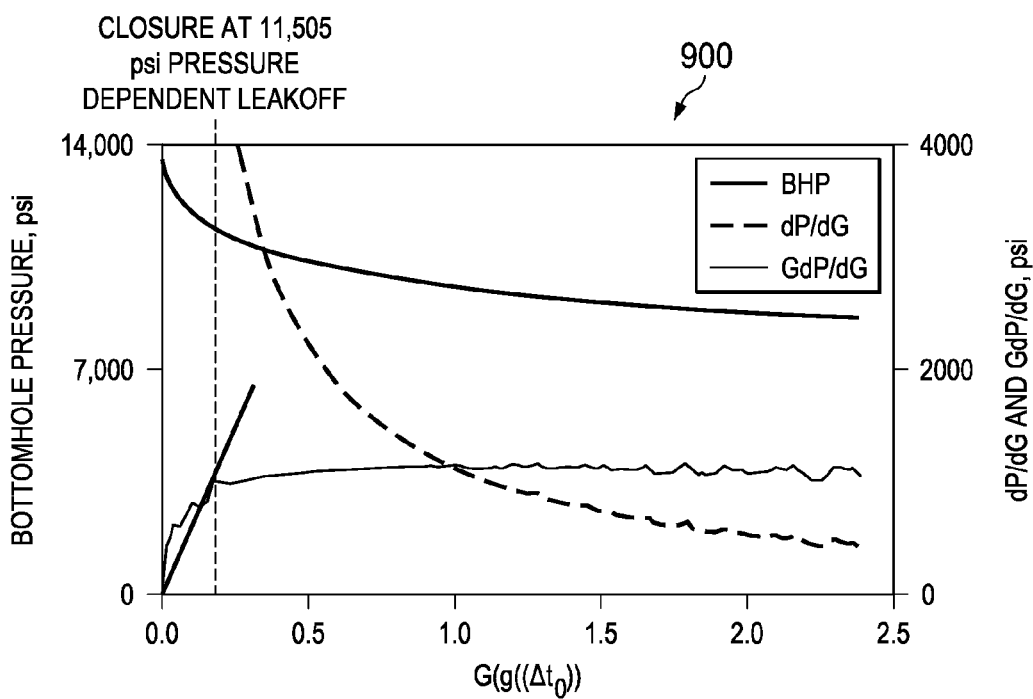
FIG. 9 is a plot of the G-function for the second example formation.
Figure 10:
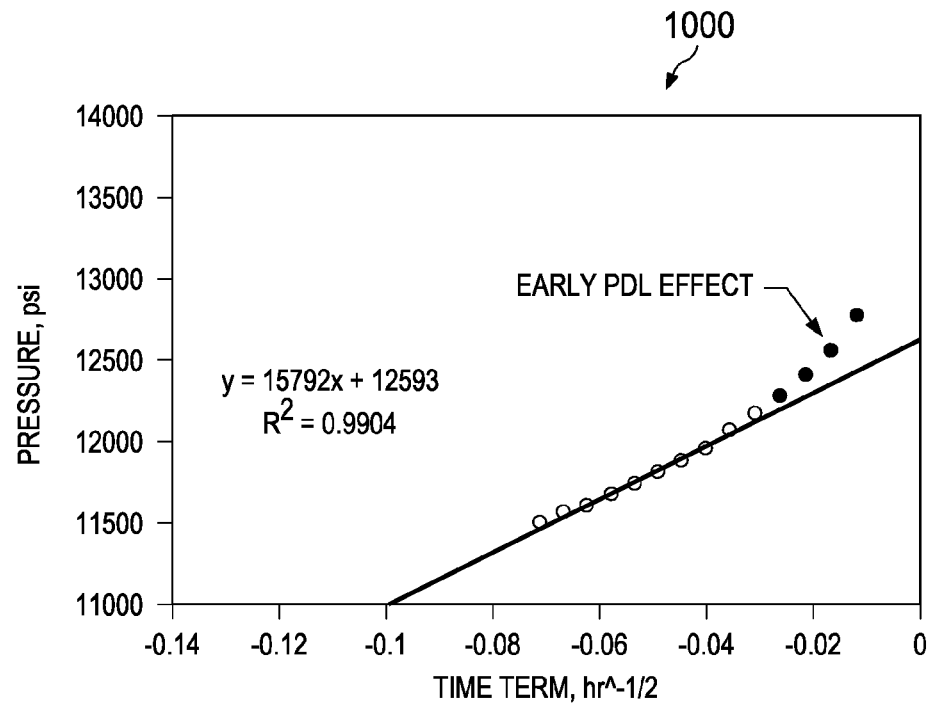
FIG. 10 is a plot of an example implementation of a before closure analysis (BCA) model of the second example formation.

Referring to FIG. 9, a plot 900 of the dimension loss function, G (i.e., the "G-function") shows the existence of pressure dependent leakoff in early time with a characteristic hump in the superposition derivative curve before fracture closure. The formation and fracture properties are listed in Table 6. The fracture length for three different geometries was calculated using Nolte-Shlyapobersky. The before closure plot 1000 is also shown in FIG. 10.

TABLE 6

FORMATION AND FRACTURE
PROPERTIES FOR EXAMPLE 2

| $c_t$ | 7.7E-05 | $psi^{-1}$ |
|---|---|---|
| $\mu_f$ | 0.0320 | cp |
| Porosity | 0.1 | — |
| Poisson's | 0.2 | — |
| E | 3.00E+06 | psi |
| $P_c$ | 11,505 | psi |
| $P_i$ | 7,750 | psi |
| $h_p$ | 27 | ft |
| $h_f$ | 40 | ft |
| $X_f$(GDK) | 30 | ft |
| $X_f$(PKN) | 37 | ft |
| $R_f$(Radial) | 47 | ft |

The slope and intercept of the straight line is shown on plot 1000. The calculation for the BCA model can be performed according to the following:

$$1.051114 \frac{r_p \Delta P_{inj} C_{Df} t_i}{c_f} \left( \frac{\phi k c_t}{\mu} \right)^{\frac{1}{2}} = 15792 \ psi*hr^{1/2}.$$

The $\Delta P_{inj}$ is calculated by using the line intercept and initial pressure; the results for permeability for three different geometries are listed in Table 7.

As it can be seen from Table 7, the values calculated for permeability based on the three example geometries range from a relatively low value of of 0.04 md for radial geometry to the 0.92 md calculated using the GDK model.

TABLE 7

BCA RESULTS FOR EXAMPLE 2

| Fracture Geometry | Storage Coefficient | Cd | Cf | K md |
|---|---|---|---|---|
| PKN | 1.37E-02 | 2.57E-02 | 2.01E-05 | 0.58 |
| GDK | 6.45E-03 | 3.08E-02 | 3.02E-05 | 0.92 |
| Radial | 3.34E-02 | 1.03E-01 | 2.03E-05 | 0.04 |

Figure 11:
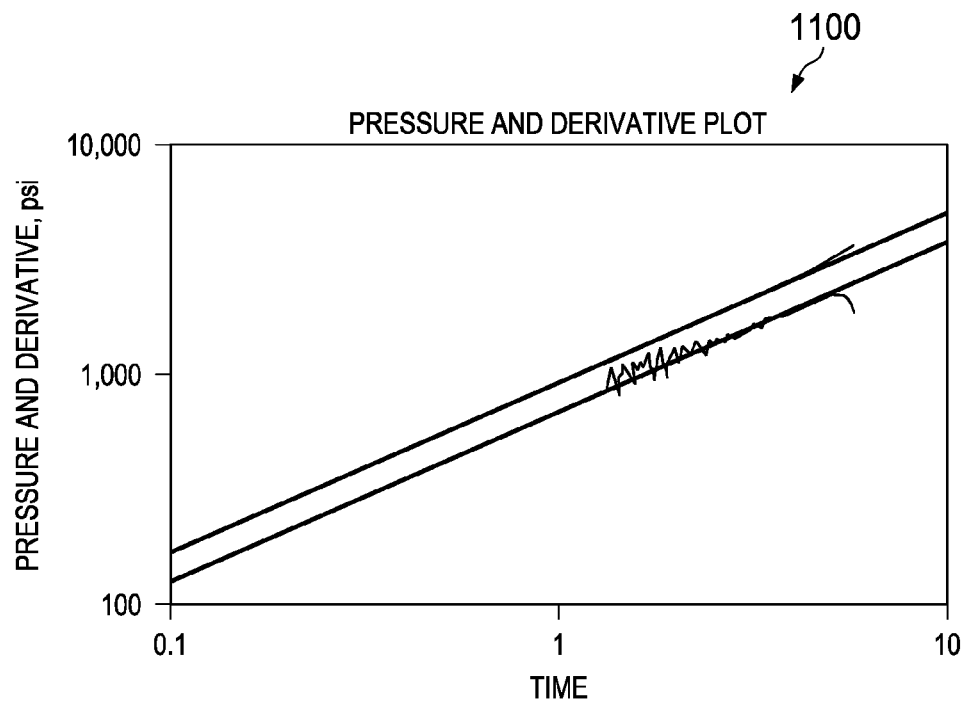
FIG. 11 is a log-log plot of an example after closure analysis (ACA) model of the second example formation.
Figure 12:
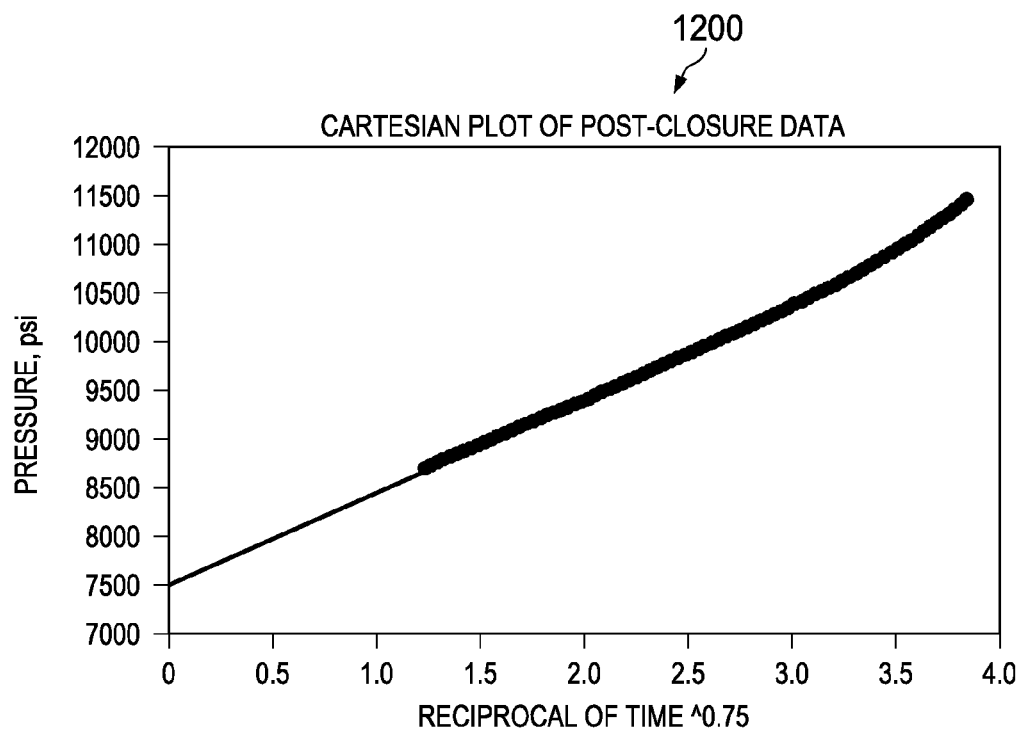
FIG. 12 is a plot of a modified Mayerhofer's BCA model of the second example formation.

For comparison, the result of ACA is shown in plots 1100 and 1200 of FIGS. 11 and 12, respectively. The existence of 0.75 slopes in the log-log plot 1000 indicates that the bilinear flow pattern dominated the reservoir flow.

As noted previously, the initial pressure is required to conduct the ACA and to plot the log-log graph. The initial pressure was obtained using a Cartesian plot of after closure data. The Cartesian plot of after closure data provides a reservoir pressure of 7,750 psi, which was used to generate the log-log plot. The intercept of log-log plot is 933 psi; using this value and according to the bilinear ACA, formation permeability could be calculated as follows:

$$k = 264.6 \frac{V}{h} \frac{\mu}{b_r} \frac{1}{(2.637 t_{ef})^{0.25}}.$$

Substituting the formation properties and intercept in the equation below results in calculation of permeability equal to 0.58 md.

$$k = 264.6 \frac{\left(\frac{7966}{42}\right)}{27} \frac{0.344}{933} \frac{1}{(2.637*0.75722)^{0.25}} = 0.5763 \ md.$$

This calculated permeability from ACA is the same value calculated by the present BCA model for a PKN geometry, which confirms the application of the present BCA model.

The BCA analysis using a modified Mayerhofer's model suggests the same calculated permeability, but for GDK geometry. The modified Mayerhofer BCA results are summarized in Table 8.

TABLE 8

MODIFIED MAYERHFOER
BCA RESULTS

| Fracture Geometry | K md |
|---|---|
| PKN | 0.02 |
| GKD | 0.59 |
| Radial | 0.46 |

Figure 13:
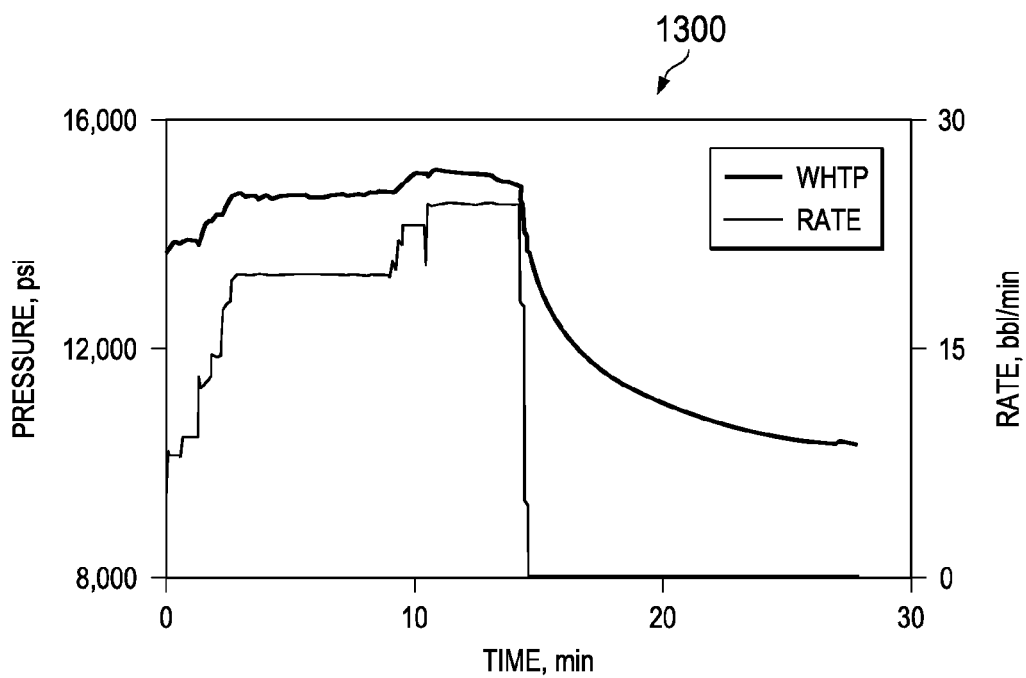
FIG. 13 is a plot of pressure versus time data obtained for a DFIT of a third example formation.

In another example, plot 1300 of FIG. 13 shows the pressure falloff data for another example formation. In this example, there is no water hammer effect, which eases the analysis and interpretation of data. This DFIT test represents the injection of 12,210 gal of linear gel with average injection rate of 18.8 bbl/min for an injection time of 928 sec. BHT was 312° F. and the kh was estimated to be 240 md-ft.

Figure 14:
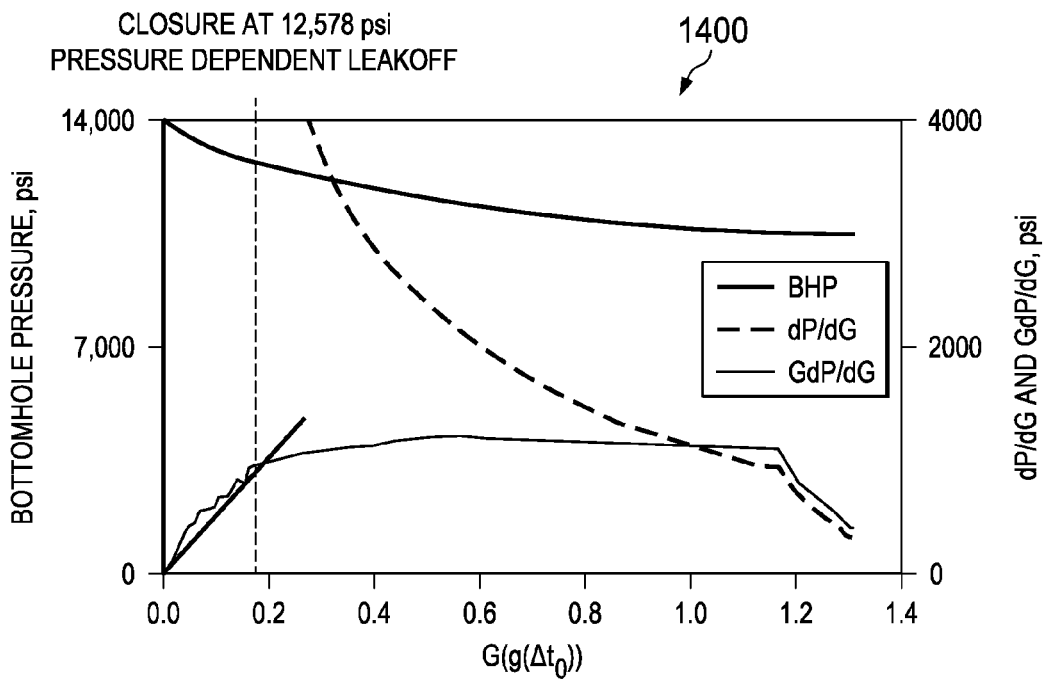
FIG. 14 is a plot of the G-function for the third example formation.

The ISIP pressure was recorded as 13,760 psi and the resulting fracture gradient was 0.97 psi/ft. The G-function graph 1400 is shown in FIG. 14; the closure pressure was observed at 12,578 psi and closure time was 874 sec after the end of injection. The characteristic hump in the G-function graph shows the existence of PDL.

With the reservoir thickness of 20 ft, it was estimated by pre-fracturing analysis that the formation permeability should be approximately 2 md. Although this permeability is fairly high, still, the present BCA model can be applied to analyze the before closure data to estimate the permeability, because, as noted in the above, the results from fluid flow solution for linear and radial flow pattern in the case of long-term approximation are fairly close in most cases.

However, in case of high formation permeability where spurt loss volume exists, the fracture length calculation might not be accurate because the fracture geometries for these examples in this paper are calculated using Nolte-Shlypobersky model, which ignores the spurt loss volume. Thus, in some implementations, the calculated results could be slightly different than what is calculated by ACA.

The formation and fracture properties are shown in Table 9. The analysis for fracture geometries of GDK, radial, and PKN are provided.

TABLE 9

FORMATION AND FRACTURE PROPERTIES FOR EXAMPLE 3
Formation Properties

| | | |
|---|---|---|
| $c_t$ | 9.5E-05 | psi$^{-1}$ |
| $\mu_f$ | 0.037 | cp |
| Porosity | 0.095 | — |
| Poisson's | 0.2 | — |
| E | 5.00E+06 | psi |
| $P_c$ | 12,578 | psi |
| $h_p$ | 20 | ft |
| $h_f$ | 67 | ft |
| $X_f$(GDK) | 38 | ft |
| $X_f$(PKN) | 47 | ft |

Figure 15:
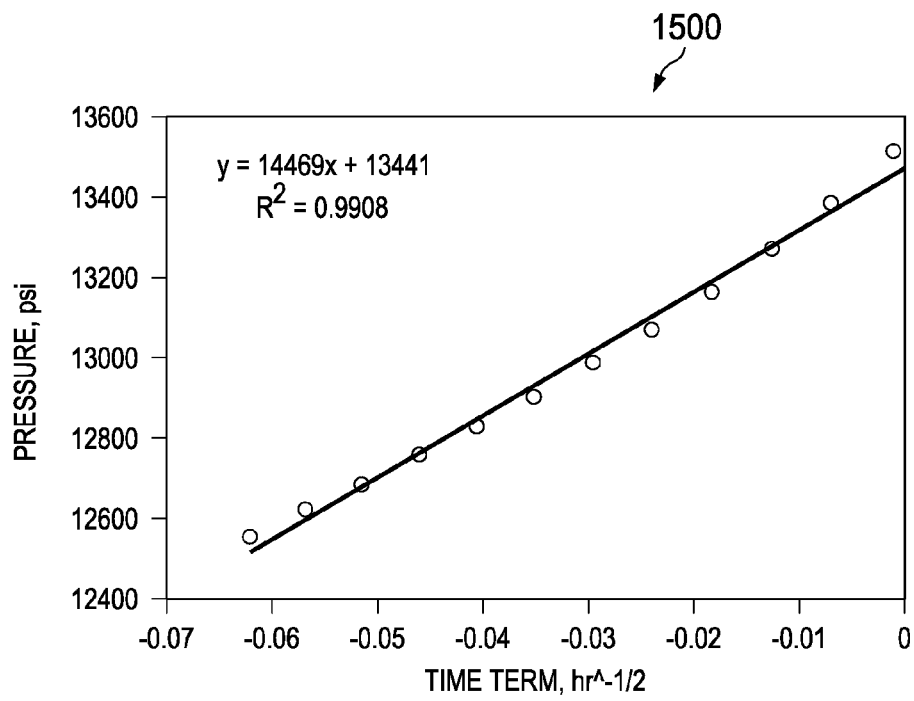
FIG. 15 is a plot of an example implementation of a before closure analysis (BCA) model of the third example formation.

A plot 1500 of the present BCA is shown in FIG. 15. Although, the existence of PDL distorts the data somewhat, the data points are still showing the straight-line pattern.

The intercept is showing the $P_{inj}$ equal to 13,441 psi, which is very close to recorded ISIP pressure during the test. This method provides a more accurate tool to calculate the ISIP pressure. The slope of the straight line is 14,469 psi.hr$^{1/2}$, the BCA results are shown in Table 10.

$$1.051114 \frac{r_p \Delta P_{inj} C_{Df} t_i}{c_f} \left( \frac{\phi k c_t}{\mu} \right)^{\frac{1}{2}} = 14469 \; psi * hr^{1/2}.$$

TABLE 10

NEW BCA MODEL RESULTS FOR EXAMPLE 3

| Fracture Geometry | Storage Coefficient | Cd | Cf | K md |
|---|---|---|---|---|
| PKN | 0.022641 | 0.050852 | 2.02067E-05 | 1.18 |
| GDK | 0.010412 | 0.035634 | 2.29417E-05 | 3.11 |
| Radial | 0.018688 | 0.042252 | 1.52529E-05 | 0.98 |

Figure 16:
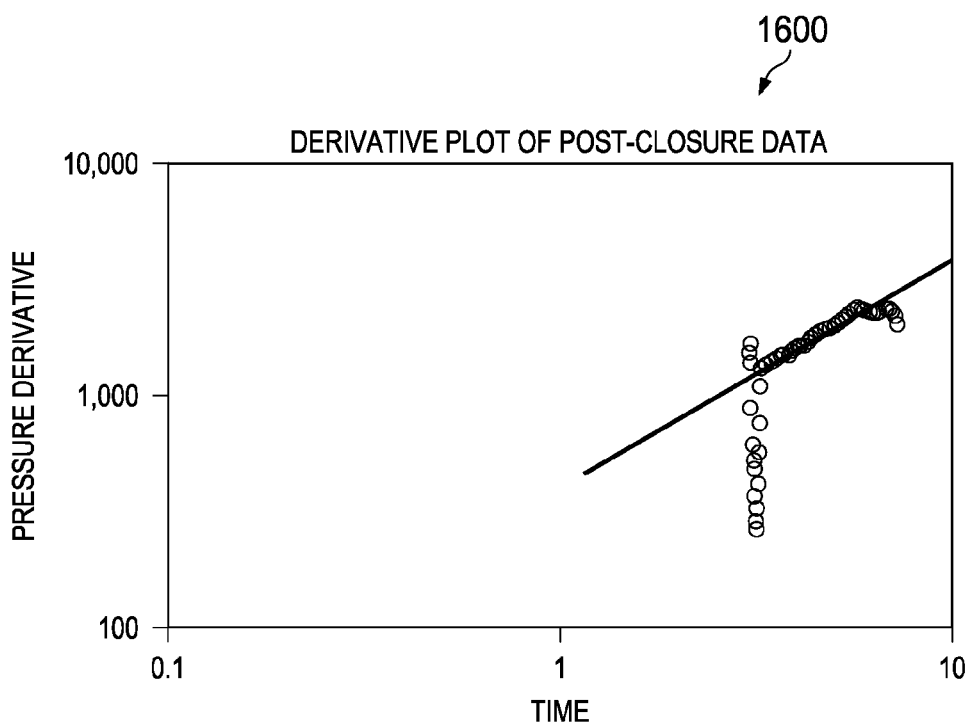
FIG. 16 is a log-log plot of an example after closure analysis (ACA) model of the third example formation.

For comparison, the result of ACA is shown in plot 1600 of FIG. 16, depicting the derivative of the pressure versus time plotted as a log-log graph.

The existence of the unit slope line again indicates the presence of the pseudo-radial flow regime. The Cartesian plot of Pressure versus reciprocal of time then was created to estimate the reservoir initial pressure, by using the equation of:

$$P_{fo} - P_i = \frac{1694.4 \; V\mu}{kh} \frac{1}{(t_i + \Delta t)}.$$

The estimated initial pressure was recorded as 9,000 psi and then the log-log plot 1500 was created to calculate the permeability. The calculation of the reservoir permeability is as follows:

$$kh = \frac{1694.4 \; V\mu}{b_r},$$

where $$kh = \frac{1694.4 \left( \frac{12120}{42} \right) * 0.0037}{420} = 4.34 \; md\text{-ft}.$$

Using the reservoir thickness of 20 ft, the permeability was calculated equal to 2.17 md.

Figure 17:
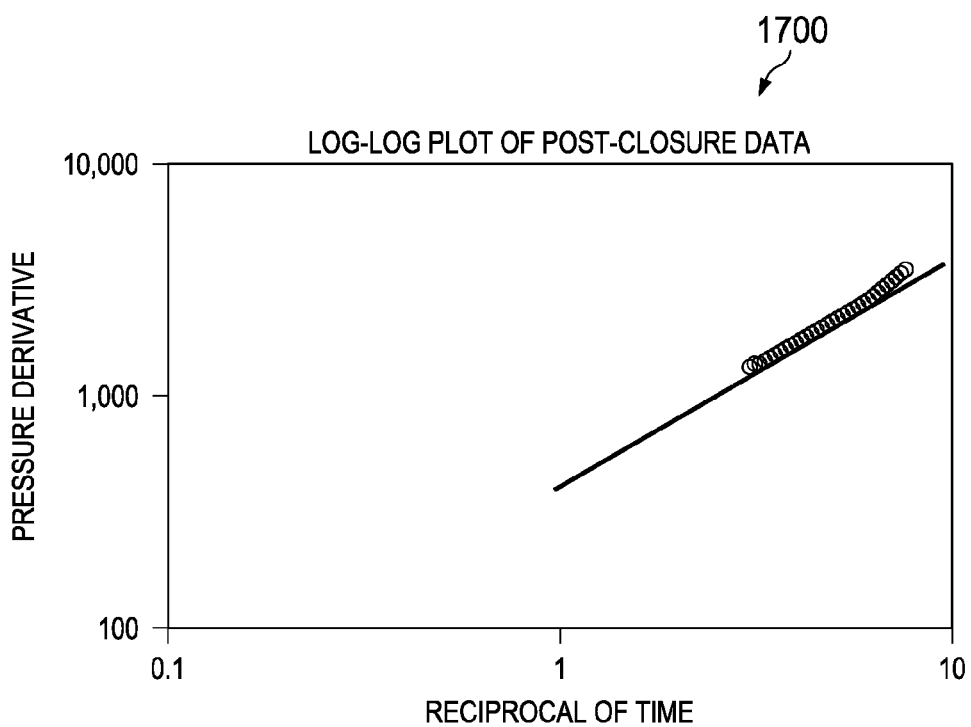
FIG. 17 is a plot of a modified Mayerhofer's BCA model of the third example formation.

In this example, the permeability calculated from ACA is slightly different than permeability calculated from the present BCA model. As discussed previously, this formation is a moderate-permeability formation, and, because this model was developed for unconventional reservoirs with low permeability and we used the long term solution from linear leakoff flow regime, there might be some error in the BCA calculated permeability because the leakoff could not be considered completely linear. However, this error should be relatively small because the results for long-term approximation using linear and radial flow regime is fairly close. The more important portion of this 0.9-md difference between ACA and BCA is related to fracture dimensions used in this example. As discussed above, fracture dimensions were calculated using the Nolte-Shlyapobersky model. The main assumption in this model is neglecting the spurt loss volume. In low-permeability formations, such as unconventional reservoirs, this assumption is valid. However, in the case of this example, where the formation permeability is moderately high, ignoring this volume will result in calculation of longer fractures. Considering a shorter fracture length of 32 ft for the GDK geometry in the new BCA model results in calculation of permeability equal to 2.20 md, which is in agreement with the ACA model, as shown in plot 1700 of FIG. 17. These results furthermore confirm the validity of the present BCA model based on the solution of fluid flow into the formation.

The analysis of the BCA using the modified Mayerhofer's model also agrees with the values presented here, which shows that, as long as the assumptions of the modified Mayerhofer's model are not extremely violated, it could provide the estimation of permeability with high accuracy.

The techniques described above can be implemented in digital electronic circuitry, or in computer software, firmware, or hardware, including the structures disclosed in this specification and their structural equivalents, or in combinations of one or more of them. For example, control module 106 can include an electronic processor that can be used to control systems for controlling pump 104 and measuring data from the instrumentation. In another example, an electronic processor can be used to analyze and process data during DFIT analysis, for instance to estimate the permeability using implementations of the above described BCA model.

The term "electronic processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Various aspects of the invention may be summarized as follows.

In general, in an aspect, a method for determining a permeability of a subterranean formation includes injecting a fluid through a well into a subterranean formation at an injection pressure sufficient to cause a fracture of the subterranean formation, shutting in the well after injecting the fluid, and before closure of the fracture, monitoring a pressure of the fluid injected into the subterranean formation after shutting in the well to provide before closure pressure data. The method further includes determining information about the permeability of the subterranean formation based on the before closure pressure data using a mathematical formula relating a measured pressure, $P_i$, at the time of shutting in, $t_i$, and the measured pressure, $P_n$, at a later time prior to closure of the fracture, $t_n$, the mathematical formula corresponding to a solution of a flow equation of the form:

$$\frac{\partial^2 P_D}{\partial x_D^2} = \frac{\partial P_D}{\partial t_D},$$

where $P_D$ is pressure, $x_D$ is a spatial dimension of the fracture, and $t_D$ is time.

Implementations of this aspect may include one or more of the following features:

The mathematical formula can be of the form:

$$A \cdot t_i \cdot k^{\frac{1}{2}} \left( \frac{1}{\sqrt{t_n}} - \frac{1}{\sqrt{t_i}} \right) + P_i = P_n$$

where k is the permeability of the formation and A is a proportionality factor.

In some implementations, $$A = B \frac{r_p \Delta P_{inj} C_{Df}}{c_f} \left( \frac{\phi c_t}{\mu} \right)^{\frac{1}{2}},$$

in which B is a constant, $r_p$ is a ratio of permeable area to fracture area of the formation, $\Delta P_{inj}$ is a change in pressure at the end of injection, $C_{Df}$ is a fracture storage coefficient, $c_f$ is a fracture compliance parameter, $\emptyset$ is a porosity of the formation, $c_t$ is a total reservoir compressibility parameter, and $\mu$ is a viscosity of the formation. In some implementations, B can be 1.051114. In some implementations, the permeability, k, can be determined according to the equation:

$$k = \left( \frac{CMc_f}{r_p \Delta P_{inj} C_{Df} t_i} \right)^2 \left( \frac{\mu}{\phi c_t} \right)$$

where C is a constant, and M is a equal to A. In some implementations, C can be 0.9514.

In some implementations, $c_f$ can correspond to a Perkins-Kern-Nordgren geometry, a Kristonovich-Geertsma-Daneshy geometry, or a Radial geometry. In some implementations, $$c_f = \frac{\pi h_f}{2E'},$$

in which $h_f$ is a height of the fracture and E' is a plane strain modulus of the formation. In some implementations, $$c_f = \frac{\pi L_f}{2E'},$$

in which $L_f$ is a length of the fracture and E' is a plane strain modulus of the formation. In some implementations, $$c_f = \frac{16 R_f}{3\pi E'},$$

in which $R_f$ is a radius of the fracture and E' is a plane strain modulus of the formation.

In some implementations, the subterranean formation can include a porous medium. In some implementations, the medium can be shale. In some implementations, the formation is an unconventional formation.

In some implementations, the before closure pressure data can correspond to the pressure of the fluid injected into the subterranean formation over a timespan of between approximately 10-3000 minutes. In some implementations, the pressure of the fluid injected into the subterranean formation can be between approximately 5000-10000 psi.

In general, in another aspect, a non-transitory computer readable medium storing instructions that are operable when executed by a data processing apparatus to perform operations for determining a permeability of a subterranean formation, the operations including obtaining before closure pressure data, the before closure pressure data corresponding to a pressure of fluid injected into a subterranean formation from a well measured after the well is shut in and before a fracture of the subterranean formation is closed. The operations further include determining information about the permeability of the subterranean formation based on the pressure measurement data, the information determined using a mathematical formula relating a measured pressure, $P_i$, at the time of shutting in, $t_i$, and the measured pressure, $P_n$, at a later time prior to closure of the fracture, $t_n$, the mathematical formula corresponding to a solution of a flow equation of the form:

$$\frac{\partial^2 P_D}{\partial x_D^2} = \frac{\partial P_D}{\partial t_D},$$

where $P_D$ is pressure, $x_D$ is a spatial dimension of the fracture, and $t_D$ is time.

Implementations of this aspect may include one or more of the following features:

The mathematical formula can be of the form:

$$A \cdot t_i \cdot k^{\frac{1}{2}} \left( \frac{1}{\sqrt{t_n}} - \frac{1}{\sqrt{t_i}} \right) + P_i = P_n$$

where k is the permeability of the formation and A is a proportionality factor.

In some implementations, $$A = B \frac{r_p \Delta P_{inj} C_{Df}}{c_f} \left( \frac{\emptyset c_t}{\mu} \right)^{\frac{1}{2}},$$

in which B is a constant, $r_p$ is a ratio of permeable area to fracture area of the formation, $\Delta P_{inj}$ is a change in pressure at the end of injection, $C_{Df}$ is a fracture storage coefficient, $c_f$ is a fracture compliance parameter, Ø is a porosity of the formation, $c_t$ is a total reservoir compressibility parameter, and μ is a viscosity of the formation. In some implementations, B can be 1.051114. In some implementations, the permeability, k, can be determined according to the equation:

$$k = \left( \frac{CMc_f}{r_p \Delta P_{inj} C_{Df} t_i} \right)^2 \left( \frac{\mu}{\emptyset c_t} \right)$$

where C is a constant, and M is a equal to A. In some implementations, C can be 0.9514.

In some implementations, $c_f$ can correspond to a Perkins-Kern-Nordgren geometry, a Kristonovich-Geertsma-Daneshy geometry, or a Radial geometry. In some implementations, $$c_f = \frac{\pi h_f}{2E'},$$

in which $h_f$ is a height of the fracture and E' is a plane strain modulus of the formation. In some implementations, $$c_f = \frac{\pi L_f}{E'},$$

in which $L_f$ is a length of the fracture and E' is a plane strain modulus of the formation. In some implementations, $$c_f = \frac{16 R_f}{3\pi E'},$$

in which $R_f$ is a radius of the fracture and E' is a plane strain modulus of the formation.

In some implementations, the subterranean formation can include a porous medium. In some implementations, the medium can be shale. In some implementations, the formation can be an unconventional formation.

In some implementations, the before closure pressure data can correspond to the pressure of the fluid injected into the subterranean formation over a timespan of between approximately 10-3000 minutes. In some implementations, the pressure of the fluid injected into the subterranean formation can be between approximately 5000-10000 psi.

In general, in another aspect, a system for determining a permeability of a subterranean formation includes an injection module adapted to inject a fluid through a well into a subterranean formation at an injection pressure sufficient to cause a fracture of the subterranean formation, and to shut in the formation after injection the fluid. The system also includes an instrumentation module adapted to, before closure of the fracture, monitor a pressure of the fluid injected into the subterranean formation after shutting in the well to provide before closure pressure data. The system also includes a data processing apparatus operable to determine information about the permeability of the subterranean formation based on the before closure pressure data using a mathematical formula relating a measured pressure, $P_i$, at the time of shutting in, $t_i$, and the measured pressure, $P_n$, at a later time prior to closure of the fracture, $t_n$, the mathematical formula corresponding to a solution of a flow equation of the form:

$$\frac{\partial^2 P_D}{\partial x_D^2} = \frac{\partial P_D}{\partial t_D},$$

where $P_D$ is pressure, $x_D$ is a spatial dimension of the fracture, and $t_D$ is time.

Implementations of this aspect may include one or more of the following features:

In some implementations, the mathematical formula can be of the form:

$$A \cdot t_i \cdot k^{\frac{1}{2}} \left( \frac{1}{\sqrt{t_n}} - \frac{1}{\sqrt{t_i}} \right) + P_i = P_n$$

where k is the permeability of the formation and A is a proportionality factor. In some implementations, $$A = B \frac{r_p \Delta_{inj} C_{Df}}{c_f} \left( \frac{\emptyset c_t}{\mu} \right)^{\frac{1}{2}},$$

in which B is a constant, $r_p$ is a ratio of permeable area to fracture area of the formation, $\Delta P_{inj}$ is a change in pressure at the end of injection, $C_{Df}$ is a fracture storage coefficient, $c_f$ is a fracture compliance parameter, Ø is a porosity of the formation, $c_t$ is a total reservoir compressibility parameter, and μ is a viscosity of the formation. In some implementations, B can be 1.051114. In some implementations, the data processing apparatus can be operable to determine the permeability, k, according to the equation:

$$k = \left( \frac{CMc_f}{r_p \Delta P_{inj} C_{Df} t_i} \right)^2 \left( \frac{\mu}{\emptyset c_t} \right)$$

where C is a constant, and M is a equal to A. In some implementations, C can be 0.9514.

In some implementations, $c_f$ can correspond to a Perkins-Kern-Nordgren geometry, a Kristonovich-Geertsma-Daneshy geometry, or a Radial geometry. In some implementations, $$c_f = \frac{\pi h_f}{2E'},$$

in which $h_f$ is a height of the fracture and E' is a plane strain modulus of the formation. In some implementations, $$c_f = \frac{\pi L_f}{E'},$$

in which $L_f$ is a length of the fracture and E' is a plane strain modulus of the formation. In some implementations, $$c_f = \frac{16 R_f}{3\pi E'},$$

in which $R_f$ is a radius of the fracture and E' is a plane strain modulus of the formation.

In some implementations, the subterranean formation can include a porous medium. In some implementations, the medium can be shale. In some implementations, the formation can be an unconventional formation.

In some implementations, the before closure pressure data can correspond to the pressure of the fluid injected into the subterranean formation over a timespan of between approximately 10-3000 minutes. In some implementations, the pressure of the fluid injected into the subterranean formation can be between 5000-10000 psi.

Other embodiments are in the following claims.

What is claimed is:

1. A method for determining a permeability of a subterranean formation, the method comprising:
   injecting a fluid through a well into a subterranean formation at an injection pressure sufficient to cause a fracture of the subterranean formation;
   shutting in the well after injecting the fluid;
   before closure of the fracture, monitoring a pressure of the fluid injected into the subterranean formation after shutting in the well to provide before closure pressure data;
   determining information about the permeability of the subterranean formation based on the before closure pressure data using a mathematical formula relating a measured pressure, $P_i$, at the time of shutting in, $t_i$, and the measured pressure, $P_n$, at a later time prior to closure of the fracture, $t_n$, the mathematical formula corresponding to a solution of a flow equation of the form:

$$\frac{\partial^2 P_D}{\partial x_D^2} = \frac{\partial P_D}{\partial t_D},$$

where $P_D$ is pressure, $x_D$ is a spatial dimension of the fracture, and $t_D$ is time.

2. The method of claim 1, wherein the mathematical formula is of the form:

$$A \cdot t_i \cdot k^{\frac{1}{2}} \left( \frac{1}{\sqrt{t_n}} - \frac{1}{\sqrt{t_i}} \right) + P_i = P_n$$

where k is the permeability of the formation and A is a proportionality factor.

3. The method of claim 2, wherein $$A = B \frac{r_p \Delta P_{inj} C_{Df}}{c_f} \left( \frac{\emptyset c_t}{\mu} \right)^{\frac{1}{2}},$$

in which P is a constant, $r_p$, is a ratio of permeable area to fracture area of the formation, $\Delta P_{inj}$ is a change in pressure at the end of injection, $C_{Df}$ is a fracture storage coefficient, $c_f$ is a fracture compliance parameter, Ø is a porosity of the formation, $c_t$ is a total reservoir compressibility parameter, and μ is a viscosity of the formation.

4. The method of claim 3, wherein $c_f$ corresponds to a Perkins-Kern-Nordgren geometry, a Kristonovich-Geertsma-Daneshy geometry, or a Radial geometry.

5. The method of claim 1, wherein the subterranean formation is comprised of a porous medium.

6. The method of claim 1, wherein the formation is an unconventional formation.

7. The method of claim 1, wherein the before closure pressure data corresponds to the pressure of the fluid injected into the subterranean formation over a timespan of between approximately 10-3000 minutes, and wherein the pressure of the fluid injected into the subterranean formation is between approximately 5000-10000 psi.

8. A non-transitory computer readable medium storing instructions that are operable when executed by a data processing apparatus to perform operations for determining a permeability of a subterranean formation, the operations comprising:
   obtaining before closure pressure data, the before closure pressure data corresponding to a pressure of fluid injected into a subterranean formation from a well measured after the well is shut in and before a fracture of the subterranean formation is closed;
   determining information about the permeability of the subterranean formation based on the pressure measurement data, the information determined using a mathematical formula relating a measured pressure, $P_i$, at the time of shutting in, $t_i$, and the measured pressure, $P_n$, at a later time prior to closure of the fracture, $t_n$, the mathematical formula corresponding to a solution of a flow equation of the form:

$$\frac{\partial^2 P_D}{\partial x_D^2} = \frac{\partial P_D}{\partial t_D},$$

where $P_D$ is pressure, $x_D$ is a spatial dimension of the fracture, and $t_D$ is time.

9. The computer readable medium of claim 8, wherein the mathematical formula is of the form:

$$A \cdot t_i \cdot k^{\frac{1}{2}} \left( \frac{1}{\sqrt{t_n}} - \frac{1}{\sqrt{t_i}} \right) + P_i = P_n$$

where k is the permeability of the formation and A is a proportionality factor.

10. The computer readable medium of claim 9, wherein $$A = B \frac{r_p \Delta P_{inj} C_{Df}}{c_f} \left( \frac{\emptyset c_t}{\mu} \right)^{\frac{1}{2}},$$

in which B is a constant, $r_p$ is a ratio of permeable area to fracture area of the formation, $\Delta P_{inj}$ is a change in pressure at the end of injection, $C_{Df}$ is a fracture storage coefficient, $c_f$ is a fracture compliance parameter, $\emptyset$ is a porosity of the formation, $c_t$ is a total reservoir compressibility parameter, and $\mu$ is a viscosity of the formation.

11. The computer readable medium of claim 10, wherein $c_f$ corresponds to a Perkins-Kern-Nordgren geometry, a Kristonovich-Geertsma-Daneshy geometry, or a Radial geometry.

12. The computer readable medium of claim 8, wherein the subterranean formation is comprised of a porous medium.

13. The computer readable medium of claim 8, wherein the formation is an unconventional formation.

14. The computer readable medium of claim 8, wherein the before closure pressure data corresponds to the pressure of the fluid injected into the subterranean formation over a timespan of between approximately 10-3000 minutes, and wherein the pressure of the fluid injected into the subterranean formation is between approximately 5000-10000 psi.

15. A system for determining a permeability of a subterranean formation, the system comprising:
   an injection module adapted to inject a fluid through a well into a subterranean formation at an injection pressure sufficient to cause a fracture of the subterranean formation, and to shut in the formation after injection the fluid;
   an instrumentation module adapted to, before closure of the fracture, monitor a pressure of the fluid injected into the subterranean formation after shutting in the well to provide before closure pressure data;
   a data processing apparatus operable to determine information about the permeability of the subterranean formation based on the before closure pressure data using a mathematical formula relating a measured pressure, $P_i$, at the time of shutting in, $t_i$, and the measured pressure, $P_n$, at a later time prior to closure of the fracture, $t_n$, the mathematical formula corresponding to a solution of a flow equation of the form:

$$\frac{\partial^2 P_D}{\partial x_D^2} = \frac{\partial P_D}{\partial t_D},$$

where $P_D$ is pressure, $x_D$ is a spatial dimension of the fracture, and $t_D$ is time.

16. The system of claim 15, wherein the mathematical formula is of the form:

$$A \cdot t_i \cdot k^{\frac{1}{2}} \left( \frac{1}{\sqrt{t_n}} - \frac{1}{\sqrt{t_i}} \right) + P_i = P_n$$

where k is the permeability of the formation and A is a proportionality factor.

17. The system of claim 16, wherein $$A = B \frac{r_p \Delta P_{inj} C_{Df}}{c_f} \left( \frac{\emptyset c C_t}{\mu} \right)^{\frac{1}{2}},$$

in which B is a constant, $r_p$ is a ratio of permeable area to fracture area of the formation, $\Delta P_{inj}$ is a change in pressure at the end of injection, $C_{Df}$ is a fracture storage coefficient, $c_f$ is a fracture compliance parameter, $\emptyset$ is a porosity of the formation, $c_t$ is a total reservoir compressibility parameter, and $\mu$ is a viscosity of the formation.

18. The system of claim 17, wherein $c_f$ corresponds to a Perkins-Kern-Nordgren geometry, a Kristonovich-Geertsma-Daneshy geometry, or a Radial geometry.

19. The system of claim 15, wherein the subterranean formation is comprised of a porous medium.

20. The system of claim 15, wherein the formation is an unconventional formation.

21. The system of claim 15, wherein the before closure pressure data corresponds to the pressure of the fluid injected into the subterranean formation over a timespan of between approximately 10-3000 minutes, and wherein the pressure of the fluid injected into the subterranean formation is between 5000-10000 psi.

* * * * *

UNITED STATES PATENT AND TRADEMARK OFFICE
CERTIFICATE OF CORRECTION

PATENT NO. : 9,556,729 B2
APPLICATION NO. : 14/429322
DATED : January 31, 2017
INVENTOR(S) : Christopher Hoss Lamei and Mohamed Yousef Soliman Page 1 of 1

It is certified that error appears in the above-identified patent and that said Letters Patent is hereby corrected as shown below:

In the Specification

In Column 5, Line 21, delete

" $C_{Df} z c_1 e^{-z_D \sqrt{z}} + C_{Df} S z \sqrt{z} c_1 e^{x_D \sqrt{z}} + \sqrt{z} c_1 e^{-x_D \sqrt{z}} \big|_{x_D=0} = \frac{1}{z} - \frac{e^{-t_{iD} z}}{z}$  (7). "

and insert --

$C_{Df} z c_1 e^{-z_D \sqrt{z}} + C_{Df} S z \sqrt{z} c_1 e^{x_D \sqrt{z}} + \sqrt{z} c_1 e^{-x_D \sqrt{z}} \big|_{x_D=0} = \frac{1}{z} - \frac{e^{-t_{iD} z}}{z}$  (7).

--

In the Claims

In Column 20, Claim 3, Line 62, after --which-- delete "P" and insert --*B*--

Signed and Sealed this
First Day of August, 2017

Joseph Matal
*Performing the Functions and Duties of the*
*Under Secretary of Commerce for Intellectual Property and*
*Director of the United States Patent and Trademark Office*